United States Patent [19]

Tanaka et al.

[11] Patent Number: 5,443,182
[45] Date of Patent: Aug. 22, 1995

[54] METHODS AND APPARATUS FOR PREPARING AND DELIVERING BONE CEMENT

[76] Inventors: Kazuna Tanaka, 5 Frontier Rd., Cos Cob, Conn. 06807; Jeffrey Kapec, 248 Wilton Rd., Westport, Conn. 06880

[21] Appl. No.: 76,557

[22] Filed: Jun. 11, 1993

[51] Int. Cl.$^6$ ............................................ A61M 5/145
[52] U.S. Cl. .................................. 222/137; 222/129; 222/145.6; 222/541.2
[58] Field of Search ........................ 525/308, 309, 265; 222/129, 145, 137, 541

[56] References Cited

U.S. PATENT DOCUMENTS

| | | | |
|---|---|---|---|
| 4,952,068 | 8/1990 | Flint | 366/377 |
| 5,051,482 | 9/1991 | Tepic | 525/309 |

FOREIGN PATENT DOCUMENTS

| | | | |
|---|---|---|---|
| 0213073 | 3/1987 | European Pat. Off. | B05C 17/00 |
| 0388106 | 9/1990 | European Pat. Off. | A61F 9/00 |
| 0503824 | 9/1992 | European Pat. Off. | A61L 25/00 |
| 2801706 | 7/1979 | Germany | A61M 3/00 |
| 8705492 | 9/1987 | Germany | A61F 2/46 |

OTHER PUBLICATIONS

Trubond, "Plastic Welder", Commercial Item, US&D as an Exhibit, produced by True Value, Inc.

*Primary Examiner*—Patrick J. Ryan
*Assistant Examiner*—Patrick R. Delaney
*Attorney, Agent, or Firm*—Joseph J. Kaliko

[57] ABSTRACT

Methods and apparatus are set forth for preparing and delivering bone cement from a powdered polymer component and a liquid monomer component by simultaneously injecting the powdered and liquid components, stored in separate component chambers, into an evacuated mixing chamber under the effect of the vacuum; by uniformly mixing the components in the mixing chamber (to thoroughly wet the powder); and by delivering the cement formed by the polymerization process, as needed in an operative setting, utilizing a single ready to use device. The uniform mix is achieved by simultaneously subjecting the contents of the component chambers to the effects of the mixing chamber's vacuum via separate one way nozzles, interconnecting the component chambers to the mixing chamber, which cause the powder to be broadcast and liquid to be sprayed into the mixing chamber. The nozzles are designed and oriented in a predetermined manner (depending on the type and quantity of the constituent bone cement components being mixed), to cause the components to interact at a preselected distance within the mixing chamber, to assure uniform powder saturation and a thorough mix which yields a homogeneous reaction product.

24 Claims, 5 Drawing Sheets

SECTION A-A

SECTION B-B

METHODS AND APPARATUS FOR PREPARING AND DELIVERING BONE CEMENT

BACKGROUND OF THE INVENTION

1. Field of the Invention

The invention relates generally to methods and apparatus for preparing and delivering a self curing bone cement formed as a polymeric reaction product after mixing a powdered polymer component with a liquid monomer component.

More particularly, the invention relates to methods and apparatus for preparing and delivering bone cement by simultaneously injecting the aforementioned powder and liquid components (previously sterilized and stored in separate component chambers), into an evacuated mixing chamber; uniformly mixing the components therein (to thoroughly wet the powder); and delivering the cement formed by the polymerization process, as needed in an operative setting, utilizing a single ready to use device.

The uniform mix is achieved by simultaneously subjecting the contents of the component chambers to the effects of the mixing chamber's vacuum via separate one way nozzles, interconnecting the component chambers to the mixing chamber, which cause the powder to be broadcast and liquid to be sprayed into the mixing chamber. The nozzles are designed and oriented in a predetermined manner (depending on the type and quantity of the constituent bone cement components being mixed), to cause the components to interact at a preselected distance within the mixing chamber, to assure uniform powder saturation and a thorough mix which yields a homogeneous reaction product.

2. Brief Description of the Prior Art

In many orthopedic surgical procedures it is necessary to employ a bonding material to set implants such as pins and artificial joints in bone. The demand for bone cement for such applications has increased in spite of the growth of cementless implant technology. This is because bone cement has distinct indications and a surgeon will usually specify a cement based upon its tensile strength and workability.

The cement employed for surgical purposes is generally a polymeric material which is prepared by copolymerization of its components as needed. Because of the necessity for a fairly quick setting material the cement is almost universally prepared by a surgical assistant during the course of the operation in the sterile field of the operating room. The preparation of the cement involves mixing the aforementioned components in a suitable vessel.

The cement is usually a (meth)acrylic material which is a reaction product of a monomer and a polymer, e.g., methylmethacrylate monomer and polymethylmethacrylate or methylmethacrylate-styrene copolymer. In order to provide a cement which has the desired properties and which has the desired fixation of the implants, it is necessary that the compounds be uniformly and thoroughly mixed so that a homogeneous reaction product is produced.

Many systems exist for the preparation and delivery of a polymethylmetacrylate bone cement formed from powdered polymer and liquid monomer components. However, the known systems have various shortcomings, to be discussed hereinafter, which make a quality cement (in terms of strength, durability, etc.), difficult to prepare.

Careful mixing is required to maximize the amount of powder that is wet and to keep out (and/or remove) as much air as possible from the mixture. Failure to achieve these two objectives can result in unpolymerized powder and/or air bubbles contaminating the final reaction product cement mixture. These contaminants have the potential for compromising the long term performance of the cement and any associated implant.

Furthermore, the known processes for mixing polymethylmetacrylate cement are often complicated by the need to deal with noxious fumes produced when the aforementioned components are mixed, and because the useful working time for the cement (time before it hardens) is short.

In spite of the aforementioned difficulties, manufacturers have made conscientious efforts to improve systems for preparing and delivering bone cement by, for example, using component mixing chambers connected to vacuum pumps to filter fumes; providing mixing paddles to try and produce a more uniform cement mixture; using compression techniques to "squeeze" out air from the mixture; using dispensing guns to eject premixed material loaded into the gun, and so on.

These known systems are inherently problematic from several reasons. Vacuum tubes must be hooked up; mixing paddles must be engaged and do not insure uniform saturation of the powder component; the noxious fumes must be drawn away from the mixing site; and any premixed cement must actually be placed into the dispensing apparatus.

Furthermore, the two components themselves must be removed from separate packaging and be placed into a mixing chamber. The separate packaging is required since the monomer and cement powder can not be sterilized in the same manner. The liquid component requires aseptic packaging, while the powder component must be gamma sterilized.

The two sterile packages are typically comprised of different structures (usually a glass vial for the liquid and a plastic packet for the powder). Furthermore, the two components have different consistencies, densities and mixing properties. All of the aforementioned factors make the critical mixing sequence difficult.

The prior art has attempted to address many of the aforementioned problems by, for example, utilizing compressive force to remove air from a cement mixture as the cement is being formed; by using a vacuum packed solid component chamber to draw the liquid component into spaces between the solid particles in an attempt to achieve a more uniform component mixture; by filtering fumes created during the reaction process, as will be explained hereinafter with reference to several issued patents which exemplify the state of the art.

In particular, Gunnarsson, in U.S. Pat. No. 4,758,096; Draenert, in U.S. Pat. NO. 4,996,601; Tepic, in U.S. Pat. No. 5,051,482; Chan, in U.S. Pat. Nos. 4,973,168 and 5,100,241; and Kindt-Larsen et al., in U.S. Pat. No. 5,114,240 (and corresponding Danish Patent Number 2355/89), are referred to hereinafter to illustrate the present state of the bone cement preparation and delivery art.

These patents are broadly directed to two types of systems. Systems that use a vacuum for the mixing process and systems that use a compressive force to mix the bone cement components.

In particular, Gunnarsson, in U.S. Pat. No. 4,758,096, issued Jul. 19, 1988, is a background reference which teaches apparatus for mixing bone cement components in a vacuum. The reference cites minimizing the potential for air remaining in the reaction product as the principal advantage of mixing the cement in an evacuated container.

The Gunnarsson reference requires that the mixing container be connected to an external vacuum source after the components of the bone cement are first placed into the mixing container. Once under a vacuum, the components are manually agitated to create the mix.

Such a system, although reducing the amount of air in the mixture by performing the mixing process in a vacuum, does little to insure that all of the powder is wet before the reaction process begins. As indicated hereinabove, failure to address this problem can result in inclusions being formed in the finished cement product as a result of unpolymerized powder being included in the mix.

Furthermore, the teachings of Gunnarsson require the use of a separate vacuum pump to evacuate the mixing chamber (once the components are placed therein), with the vacuum pump requiring manual hookup and a start up delay before the mixing process can begin. This delay takes valuable time away from being able to achieve a thorough mix since the reactive components have already been placed together (and are reacting to one another) in the mixing chamber.

Further examples of techniques for mixing bone cement components in a vacuum are described by Tepic, in U.S. Pat. No. 5,051,482; and Chan, in U.S. Pat. Nos. 4,973,168 and 5,100,241.

Tepic, in U.S. Pat. No. 5,051,482, issued Sep. 24, 1991, describes methods and apparatus for preparing a self-curing two-component powder liquid bone cement using a vacuum packed powder chamber into which monomer is introduced. The Tepic system was designed to eliminate the need for mechanical stirring (as required by Gunnarsson) which, even under a vacuum, has been found to produce air inclusions that weaken the finally hardened cement mass.

Nevertheless, Tepic, like Gunnarsson, did not solve or even address the problem of insuring that all of the powder is thoroughly saturated with the liquid bone cement component before the reaction process begins.

Chan, in U.S. Pat. No. 5,100,241, issued Mar. 31, 1992, and U.S. Pat. No. 4,973,168, teaches a two-component bone cement mixing system comprising a cartridge mixer having an interior volume containing a first predetermined quantity of a free-flowing, powdery, solid bone cement component under vacuum pressure, an ampoule containing a second predetermined quantity of a liquid bone cement component, and a fluid transfer mechanism for fluidically connecting the cartridge mixer and ampoule.

The two-component bone cement mixing system described by Chan allows in vacuo mixing of liquid monomeric and solid polymeric bone cement components without air being incorporated into the mixture and prevents the passage of air into the cartridge mixer during and/or after monomeric transfer. The mixing process itself is carried out by causing reciprocating motion of a mixing element within the cartridge mixer.

Chan however, like the other references cited hereinabove, fails to teach, claim or even suggest methods and apparatus which insure that all of the powder is thoroughly saturated with the liquid bone cement component before the reaction process begins.

Furthermore, Chan's system for admixing bone cement components under vacuum pressure contemplates using a predetermined degree of chilling to control the rate of hardening of the cement, and subsequent pressurizing of the admixture to help inhibit entrainment of gaseous materials in the cement mix.

Accordingly, the system contemplated by Chan not only fails to solve the problem of thoroughly wetting the powder, but is unduly complicated to operate.

Draenert, in U.S. Pat. No. 4,996,601, issued Oct. 30, 1990, describes apparatus for mixing and applying bone cement using an evacuatable bone cement syringe. The syringe system described includes a container for receiving the bone cement prior to its application, a pressure generating apparatus for precompressing the bone cement in the container; and a bell, comprising a vacuum tube, placed over the container (and held by a flange) so that the gases which escape during the process of decompression can be sucked off to reduce the porosity of the bone cement being applied.

It should be noted that the vacuum used in the Draenert system is for outgassing purposes (not for mixing the bone cement components as described by the other references cited hereinbefore), and that Draenert uses compressive force to squeeze air out from the cement mixture. Furthermore, Draenert completely fails to teach, claim or even suggest how to solve the aforementioned uniform mixing (thorough powder saturation) problem recited hereinbefore.

Finally, the present state of the art can be more fully appreciated with reference to an alternate approach to using a vacuum to mix bone cement described by Kindt-Larsen et al., in U.S. Pat. No. 5,114,240, issued May 19, 1992 (also described in corresponding Danish Patent Number 2355/89).

According to Kindt-Larsen et al., a paste like material is provided by a mixing device that includes a first cylinder for containing a powdered component and a second cylinder for containing a liquid component. The first cylinder has a closed first end and an opposite second end provided with venting means. The second cylinder has a closed first end and an opposite second end sealingly receiving the closed first end of the first cylinder together in a piston-like manner.

The device also includes means for communicating between the inner spaces of the first and second cylinders through the closed first end of the first cylinder, whereby liquid from the first cylinder is injected into interstices defined between the powdered component contained in the first cylinder for providing a paste-like cementitious material when the first cylinder is forced into the second cylinder.

The Kinde-Larsen et al. device operates by using pressure developed by a caulking gun to force the isolated powder and liquid components together. In particular, liquid monomer is forced through the stored powder removing air from the powder compartment. The air and gasses developed during the polymerization process are vented through an activated carbon filter. Both the air and fumes are expelled by compressing the two components together.

As indicated hereinbefore, systems like the one disclosed in the Kindt-Larsen et al. reference are prone to produce cement having inclusions caused by entrapped air bubbles not removed by the applied compressive force and inclusions caused by unpolymerized powder.

Furthermore, the type of system described by Kindt-Larsen et al., requires fumes be expelled and filtered while the mixing process takes place; requiring a charcoal filter to absorb the fumes and requiring the use of a relatively unreliable force (a manually applied compressive force), to mix the monomer and powder, and to squeeze out gasses.

In view of the state of the art as illustrated by the aforementioned references, it would be desirable to provide methods and apparatus which reduce the potential for unpolymerized powder contaminating the cement mixture formed as a reaction product to the aforementioned powdered and liquid bone cement components.

To this end it would be desirable to provide methods and apparatus which produce a uniform powder/monomer mix, with the monomer wetting as much powder as possible before polymerization begins to thereby improve cement durability.

It would be further desirable to provide methods and apparatus which not only thoroughly wet the powder with the liquid monomer component, but which also keep, as well as remove, as much air as possible out of the resulting reaction product cement mixture to minimize the potential for air bubble inclusions in the reaction product to further increase cement durability.

Still further, it would be desirable to provide methods and apparatus which do not require the use of vacuum pumps, vacuum hoses, separate venting systems, filters, etc., to deal with the venting of noxious fumes and other gases produced when the aforementioned components are mixed.

Further yet, it would be desirable to provide methods and apparatus which enable bone cement to be prepared using a single ready to use device not requiring the addition of bone cement components, vacuum hookups, etc., which maintains the integrity of the sterile bone cement components throughout the cement preparation operation and which is designed to cooperate with a cement delivery unit to complete the cement preparation and delivery process.

It would also be desirable to provide methods and apparatus for preparing bone cement which do not require the evacuation of air from either one or both vehicles (packages, vials, component storage compartments, etc.), for storing the aforementioned sterile bone cement components and which do not require that the aforementioned reactive components be brought together prior to performing the mixing operation per se.

SUMMARY OF THE INVENTION

Accordingly, it is an object of the invention to provide methods and apparatus which reduce the potential for unpolymerized powder contaminating the cement mixture formed as a reaction product to the aforementioned powdered and liquid bone cement components.

In furtherance of this objective, it is another object of the invention to provide methods and apparatus which produce a uniform powder/monomer mix having as much powder as possible saturated by the liquid monomer before polymerization begins.

A further object of the invention is to provide methods and apparatus which not only thoroughly wet the powder with the liquid monomer component, but which also keep, as well as remove, as much air as possible out of the resulting reaction product cement mixture.

Still further, it is an object of the invention to provide methods and apparatus which do not require the use of vacuum pumps, vacuum hoses, separate venting systems, filters, etc., to venting noxious fumes and other gases produced when the aforementioned components are mixed.

Further yet, it is an object of the invention to provide methods and apparatus which enable bone cement to be prepared using a single ready to use cement preparation device not requiring the addition of bone cement components, vacuum hookups, etc., and which maintains the integrity of the sterile bone cement components throughout the cement preparation operation.

Yet another object of the invention is to provide a cement delivery capability by utilizing a standard, commercially available caulking gun in cooperation with the aforementioned single ready to use cement preparation device, to complete the cement preparation and delivery process.

Still further objects of the invention are to provide methods and apparatus for preparing and delivering bone cement which do not require the evacuation of air from either of the containers in which the aforementioned sterile components are stored and which do not require that reactive components be brought before the mixing process per se begins.

According to one aspect of the invention a vacuum is used to draw both components into a separate mixing chamber in a manner which thoroughly saturates the powder as part of the mixing process.

A mixing device for mixing a powdered and a liquid component in accordance with this first aspect of the invention comprises: (a) a first evacuated container; (b) a second container containing the powdered component; (c) a third container containing the liquid component; and (d) means for simultaneously connecting the aforementioned second and third containers to the first container, and which allows the powdered and liquid components to be simultaneously drawn into the first container by the vacuum therein.

According to a further aspect of the invention, a method for mixing a powdered component and a liquid component comprises the steps of: (a) evacuating a first container; (b) providing a second container containing the liquid component and a third container containing the powdered component; and (c) simultaneously connecting the second and third containers to the first container after the evacuation thereof allowing the powdered and liquid components to be simultaneously drawn into the first container.

A further process contemplated by the invention is a method (and corresponding apparatus) for preparing and delivering a self curing bone cement formed as a polymeric reaction product when a powdered polymer component is mixed with a liquid monomer component, comprising the steps of: (a) storing the powdered polymer component and the liquid monomer component in separate component chambers; (b) simultaneously injecting the powdered polymer component and the liquid monomer component into an evacuated mixing chamber; and (c) uniformly mixing the components in the mixing chamber saturating the powdered polymer component with the liquid monomer component.

In accordance with this aspect of the invention the step of simultaneously injecting further comprises the step of simultaneously subjecting the contents of the separate component chambers to the effects of the mixing chamber vacuum utilizing means which simultaneously open separate passageways between each of the component chambers and the evacuated mixing chamber.

Yet another process contemplated by the invention is a method for saturating a predetermined quantity of a powdered component with a predetermined volume of a liquid component as part of a component mixing process, comprising the steps of: (a) simultaneously injecting the powdered component and the liquid component into a mixing chamber utilizing a vacuum injection system including diffusion means to broadcast the powdered component and spray the liquid component into the chamber; and (b) orienting the diffusion means so that the powdered component and the liquid component interact at a predetermined distance within the chamber.

A still further aspect of the invention is directed to a plunger head for use as part of a system for mixing a powdered component, stored in a first chamber attached to the proximate end of the plunger head, with a liquid component, stored in a second chamber attached to the proximate end of the plunger head, within an evacuated mixing chamber into which the distal end of the plunger head extends, comprising: (a) means for simultaneously injecting the contents of the first and second component chambers into the mixing chamber vacuum; and (b) means for uniformly mixing the powdered component and the liquid component within the mixing chamber thereby saturating the powdered component with the liquid component.

According to this aspect of the invention the means for simultaneously injecting further comprises means for simultaneously subjecting the contents of the first and second component chambers to the effects of the mixing chamber vacuum, which in turn includes the combination of timing step means, seal piercing means and component diffusion means to simultaneously open (a) a first passageway through said plunger head between the first component chamber and the evacuated mixing chamber, and (b) a second passageway through the plunger head between the second component chamber and the evacuated mixing chamber.

The invention is also directed to products of the aforementioned processes.

The invention features methods and apparatus for preparing bone cement, and other mixtures of powdered and liquid components that need to be uniformly mixed, utilizing a single ready to use device that includes a vacuum injection system designed to increase cement durability. No separate attachment of vacuum hoses or separate venting system for air and/or fumes are needed to practice the invention.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

Figure 1:
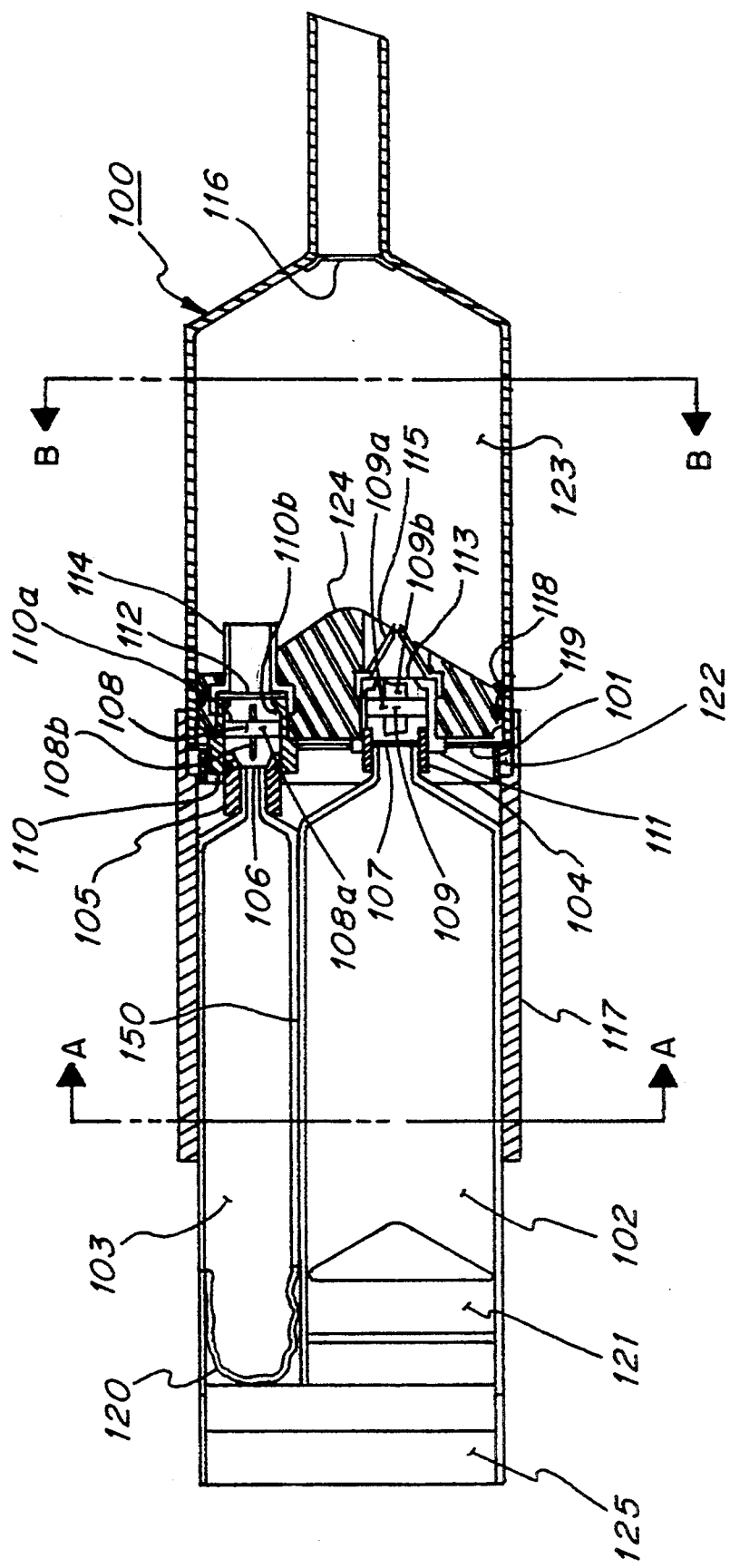
FIG. 1 is a partial elevational sectional view of an illustrative bone cement preparation and delivery device contemplated by the invention. The device is shown in a ready for use state.

An illustrative bone cement preparation and delivery device which incorporates the teachings of a preferred embodiment the invention, and which may be used to illustrate various aspects of the invention which were described hereinabove, is depicted in FIG. 1. The device shown in FIG. 1 is depicted in a ready for use state.

In particular, FIG. 1 shows a set of components that in the depicted combination (forming device 100) may be used to: (a) store a powdered polymer bone cement component (or more generally any powdered component of a two component mixture) and a liquid monomer bone cement component (or more generally any liquid component of a two component mixture), in separate component chambers; (b) perform a time sequenced, staged release of the powder and monomer into an evacuated mixing chamber into which the stored powder and liquid components are simultaneously injected; and (c) uniformly mix the components in the mixing chamber, saturating the powdered polymer component with the liquid monomer component to minimize the potential for inclusions that could otherwise form in the cement.

The components depicted in the illustrative embodiment of the invention depicted in FIG. 1 are: primary vacuum seal 101; powder chamber 102; monomer chamber 103; inner membrane mounting block 104 associated with powder chamber 102; inner membrane mounting block 105 associated with monomer chamber 103; inner membrane seal 106 for monomer chamber 103; inner membrane seal 107 for powder chamber 102; hollow needle knife blade assembly 108, including knife blade collar 108a and knife blade tube 108b; hollow knife blade assembly 109, including knife blade collar 109a and knife blade tube 109b; knife blade collar with timing step 110 associated with monomer chamber 103; timing step ridge 110a projecting into the lumen of knife blade assembly 108; knife blade assembly retainer ridge 110b; knife blade collar with timing step 111 associated with powder chamber 102; outer membrane seal 112 associated with the monomer component, for sealing off evacuated mixing chamber 123 listed hereinbelow; outer membrane seal 113 associated with the powdered component, also for sealing off evacuated mixing chamber 123; monomer component diffuser 114; powdered component diffuser 115; membrane seal 116 located at the distal end of mixing chamber 123; knife blade mounting collar 117; scraper blade 118; 0-ring plunger seal 119; flexible bladder 120; moving stopper 121; knife blade 122; and evacuated mixing chamber 123; plunger head 124; and compression block 125.

Figure 1A:
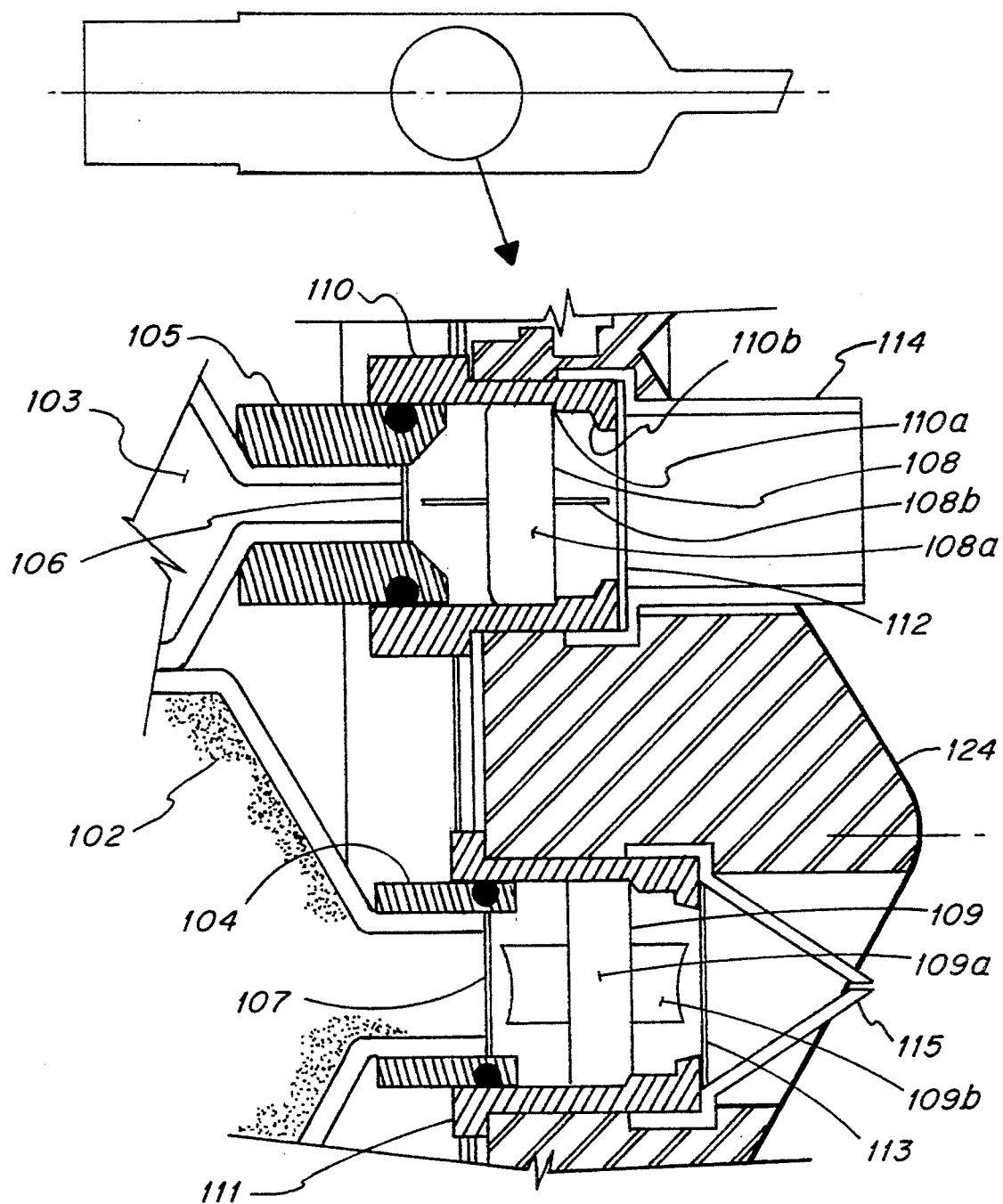
FIG. 1A is an exploded view of the knife blade assemblies and knife blade collars with timing steps depicted in FIG. 1.
Figure 2:
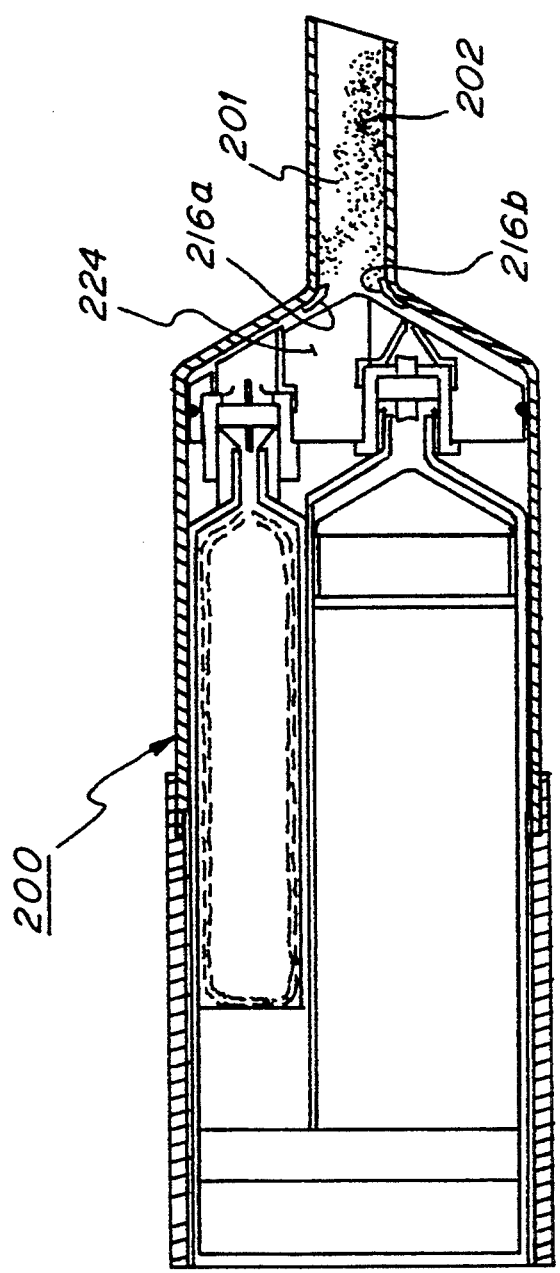
FIG. 2 is a partial elevational sectional view of the device depicted in FIG. 1 after the cement has been prepared and been substantially dispensed from the device.
Figure 3:
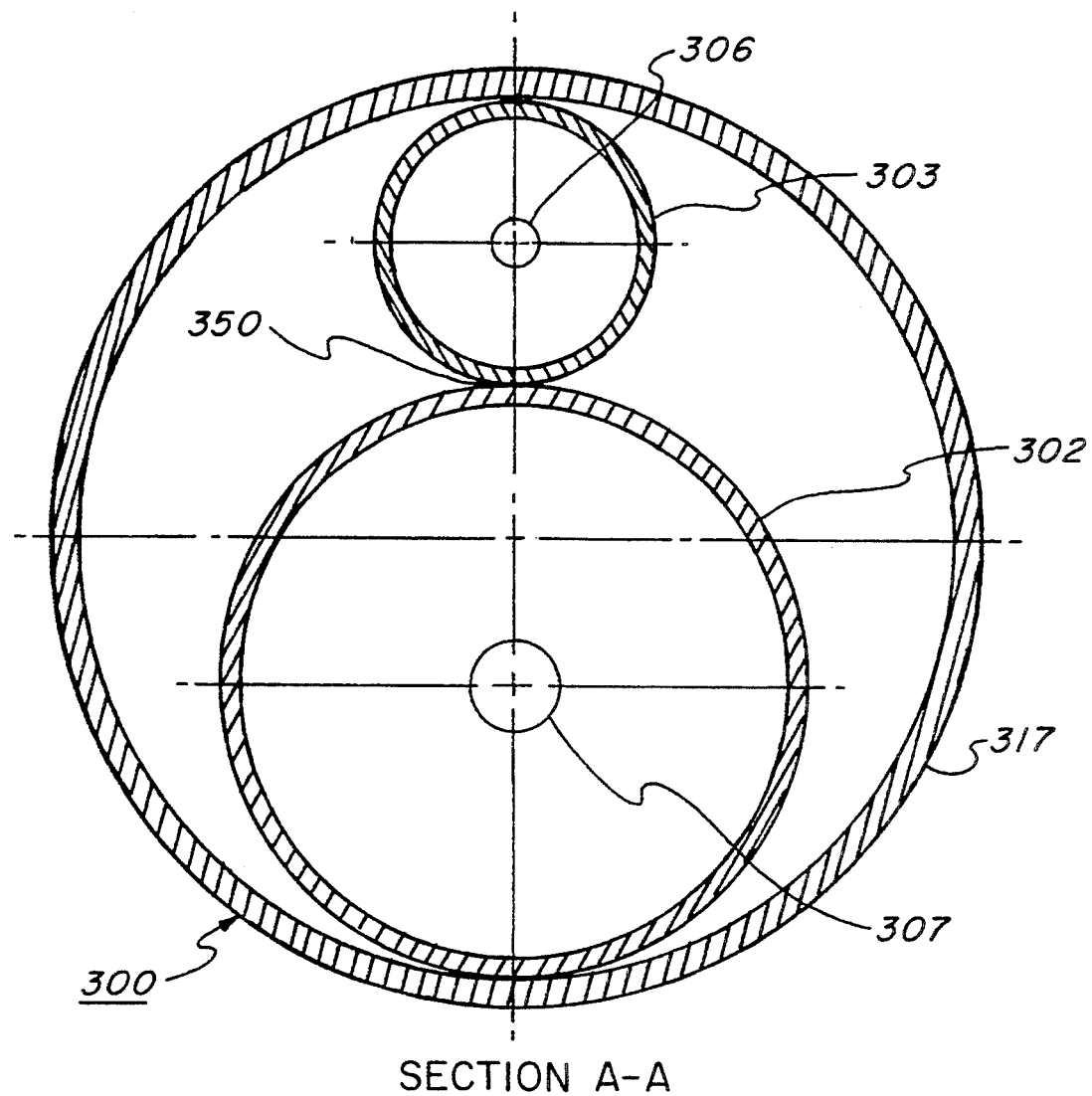
FIG. 3 is a cross sectional view of the device depicted in FIG. 1, taken along section line A—A, illustrating the orientation of the monomer and powder chambers with respect to each other and the knife blade collar contemplated by the invention.
Figure 4:
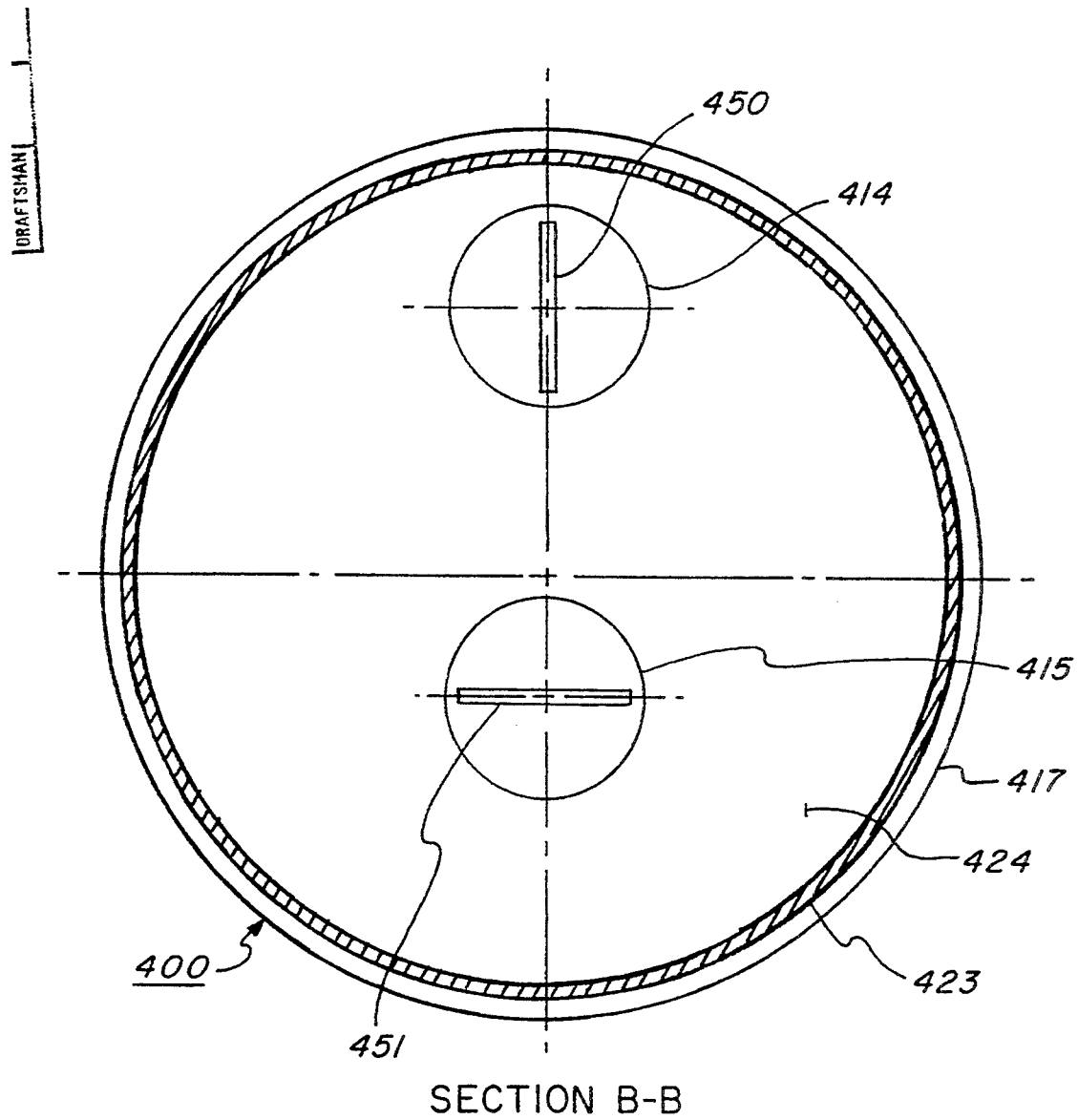
FIG. 4 is a cross sectional view of the device depicted in FIG. 1, taken along section line B—B, illustrating the orientation of the monomer and powder diffuser nozzles incorporated in the plunger head contemplated by the invention, with the view of the plunger head being that seen from the vacuum chamber side of the device looking back toward the base of the aforementioned knife blade collar.

The respective function and of each of the aforementioned components and how they interact to accomplish the objectives of the invention as recited hereinbefore, will now be set forth in detail with further reference to FIG. 1, along with reference to FIGS. 2-4. FIG. 1A may also be referred to for an exploded view of the knife blade assemblies and knife blade collars with timing steps depicted in and described with reference to FIG. 1.

It is assumed, for the sake of illustration only, that a self curing bone cement formed as a polymeric reaction product when a powdered polymer component is mixed with a liquid monomer component, is being prepared for delivery during an operation, such as an operation to set an artificial joint.

It is also assumed that the components shown in FIG. 1 have been assembled as shown and include a sterile powdered polymer component stored in a sterile powder chamber 102, and a sterile liquid monomer stored in sterile monomer chamber 103. Both chambers could, for example, be fabricated using molded materials, such as polyethylene.

Techniques for introducing these components into component chambers such as chambers 102 and 103, and insuring that the components are sterile, are well known by those skilled in the art. Accordingly, such techniques will not be further discussed herein since they do not constitute a part of the invention per se.

What is new, according to one aspect of the invention, are the steps of storing the powdered polymer component and the liquid monomer component in separate component chambers and then simultaneously injecting the stored components into an evacuated mixing chamber in which they are uniformly mixed to thoroughly saturate the powdered polymer component with said liquid monomer component. These steps, along with others that insure that a durable cement product is readily prepared and delivered in an operative setting, will now be described in detail (along with suitable apparatus for performing these steps), with reference to FIG. 1.

To start the preparation and delivery sequence, powder chamber 102 and monomer chamber 103, preferably joined together tangentially along their exterior surfaces as shown in FIG. 1 at 150, are pushed forward from their initial positions as depicted in FIG. 1, by, for example, manually depressing block 125.

It is intended that the chambers traverse forward in unison and that as the two chambers move forward they push the membrane mounting blocks 104 and 105, together with inner membrane seals 107 and 106 respectively, against knife blade tubes 109b and 108b forming a part of hollow knife blade assemblies 109 and 108 respectively. This action is designed to cause the inner membrane seals to be ruptured completing the first stage of a two step operation to simultaneously subject the stored components to the effects of the vacuum in evacuated mixing chamber 123.

According to a preferred embodiment of the invention, the aforementioned mounting blocks 104 and 105 may, for example, be fabricated using molded materials, such as polyethylene. Additionally, according to a preferred embodiment of the invention, all seals described herein may be fabricated by, for example, utilizing a co-laminate or single layer film.

It should be noted that, according to a preferred embodiment of the invention, knife blade assembly 108 includes a knife blade collar 108a and a hollow "syringe like" knife blade tube, 108b. A first piercing edge on the proximal end of knife blade tube 108b functions to rupture seal 106 when mounting block 105, shown carrying seal 106, is pushed forward into tube 108b in the manner described hereinabove.

Collar 108a may, for example, be fabricated using a molded material such as polyethylene. Knife blade tube 108b may, for example, be metallic, having sharp notched ends designed to rupture and retain portions of the seals the ends come in contact with.

The result rupturing seal 106 is to begin forming a passageway for the liquid monomer to enter evacuated mixing chamber 123. The passage way will be completed, as will be described in detail hereinafter, after seal 112 is ruptured by a second piercing edge located on the distal end of knife blade tube 108b.

Similarly, it should be noted that, according to a preferred embodiment of the invention, knife blade assembly 109 includes a knife blade collar 109a, and a larger (compared knife blade tube 108b), preferably rounded, knife blade 109b, which has a sufficient inner diameter to allow a predetermined quantity of powder to be drawn into evacuated mixing chamber 123 when a passage between powder chamber 102 and mixing chamber 123 is eventually opened in the manner to be described hereinafter.

Collar 109a may, like collar 108a, be fabricated using a molded material such as polyethylene. Knife blade tube 109b may (for example), like knife blade tube 108b, be metallic, having sharp notched ends designed to rupture and retain portions of the seals the ends come in contact with.

A first piercing edge on the proximal end of knife blade tube 109b functions to rupture seal 107 when mounting block 104, shown carrying seal 107, is pushed forward into tube 109b in the manner described hereinabove. The result of this action is to begin forming a passageway for the powdered polymer to enter evacuated mixing chamber 123. The passageway will be completed, as will be described in detail hereinafter, after seal 113 is ruptured by a second piercing edge located on the distal end of knife blade tube 109b.

The second stage of the two step operation to simultaneously subject the stored components to the effects of the vacuum in evacuated mixing chamber 123, begins as hollow knife blade assemblies 108 and 109 are push forward, toward outer membrane seals 112 and 113, by the tips of mounting blocks 104 and 105. This takes place as continued pressure is applied to block 125 at a time after seals 106 and 107 are ruptured. Seals 112 and 113 are designed to isolate the contents of the component chambers from the effects of evacuated mixing chamber 123 until such time as the seals are simultaneously ruptured by knife blade assemblies 108 and 109.

According to the illustrative embodiment of the invention being set forth with reference to FIG. 1, the knife blades are intended to move forward in unison and, after a split second delay — caused by the knife blade collar with timing steps 110 and 111, the second piercing edges of knife blade tubes 108b and 109b simultaneously rupture outer membranes 112 and 113.

According to a preferred embodiment of the invention, the timing step function may be realized by creating a resilient ridge on each of the knife blade collars with timing steps, with each ridge projecting into the lumen of the knife blade assembly (in particular, into the path of each knife blade collar), so that it keeps the knife blade assemblies from traversing forward until sufficient pressure is applied on the mounting blocks pushing against the knife blade collars during the second stage of the two stage operation described hereinabove. A portion of one such ridge, ridge 110a, is shown in FIG. 1. Ridge 110a is designed to come in contact with the side of knife blade collar 108a facing evacuated mixing chamber 123.

Alternatively, the invention contemplates the use of resilient knife blade collars which give way when forced against rigid timing step ridges formed in the knife blade collar timing steps, thereby allowing the knife blade collars to move forward at the appropriate time.

The purpose of ridge 110a (and a corresponding ridge extending from knife blade collar with timing step 111), is to prevent the knife blades from penetrating seals 112 and 113 before the powder/monomer seals (106 and 107) are broken. To insure a uniform mix, timing is extremely important and the discharge sequence is intended to be controlled by the aforementioned timing steps or means which perform the equivalent sequenced discharge function.

According to a preferred embodiment of the invention, a further ridge is fabricated on each knife blade collar with timing step, exemplified by the knife blade assembly retainer ridge 110b shown in FIG. 1. The purpose of ridge 110b is to prevent knife blade collar 108a from interfering with the operation of monomer component diffuser 114. A similar ridge is contemplated for knife blade collar with timing step 111 to prevent knife blade collar 109a from interfering with the operation of powder component diffuser 115.

It should be noted that the aforementioned knife blade collars with timing steps may also serve as fixture blocks when assembling device 100.

After seals 112 and 113 are ruptured, the vacuum in evacuated mixing chamber 123 pulls the powder and monomer from their respective chambers. As the powder and monomer is evacuated from chambers 102 and 103 respectively, the component volume withdrawn is displaced by powder plunger 121 and monomer bladder 120. This displacement prevents air from entering into the mixture.

Powder and monomer withdrawn from their respective chambers pass through the passage ways in hollow knife blade tubes 108b and 109b, and through the one way duckbill valves/diffuser ports shown in FIG. 1 (sometimes referred to herein as diffuser ports). These ports are indicated in FIG. 1 as monomer component diffuser 114 and powdered component diffuser 115.

It should be noted, as indicated hereinabove, that the knife blade tubes are, according to a preferred embodiment of the invention, designed to keep any portion of the seals they rupture from interfering with the flow of components through the knife blade tubes.

According to a preferred embodiment of the invention, one-way valve/diffuser ports 114 and 115 are designed to serve three principal functions. They should provide controlled release, injection and uniform distribution of the powder and monomer into the vacuum chamber; they should insure that the monomer will not polymerize the powder around the powder outlet, which would occlude the powder and prevent full release of the powder in powder chamber 102; and the duckbill valve should function to prevent the mixture of powder and monomer from traveling back into the powder/monomer chambers as the mixture is dispensed from the mixing chamber.

The design of one-way valve/diffuser ports to perform the aforementioned functions is well within the purview of those skilled in the art and does not constitute a part of the invention per se. The one-way valve/diffuser ports are, according to a preferred embodiment of the invention, made of silicon to achieve a durometer that supports the performance of the diffusion and backflow sealing functions described hereinabove.

It should be noted, however, that the aforementioned controlled release, injection and uniform distribution of the powder and monomer into the vacuum chamber is designed to produce a uniform mix in which the powdered component is thoroughly wet by the liquid component. This may be accomplished, according to a preferred embodiment of the invention, by orienting both one-way valve/diffuser ports (also referred to herein as "diffusion means"), so that the powdered component and the liquid component interact at a predetermined distance within evacuated mixing chamber 123.

The predetermined distance referred to hereinabove is a variable which may be determined empirically based on such factors as the amount and type of liquid and powder being mixed, the design of the one-way valve/diffuser ports used, the shape of the mixing chamber, etc. Independent of these factors, the objective is the same; namely, to saturate the maximum amount of powder possible with the liquid component.

Continuing with the description of the methods and apparatus contemplated by the invention, as indicated hereinabove, the powder and monomer are simultaneously injected and mixed together in evacuated mixing chamber 123 after seals 112 and 113 are simultaneously ruptured.

According to a one embodiment of the invention, after this procedure is completed (in most bone cement applications taking 2-4 seconds), the entire assembly depicted in FIG. 1 is then agitated (such as by manually shaking cartridge up and down), to ensure thorough mixing of the two components.

For most bone cement applications the user should wait 60-180 seconds before taking the steps described hereinafter for compressing the mixture to complete the mixing process and beginning a mixture dispensing phase in which the cement is delivered, as needed, in the operative setting. It should be noted that the end user can control the viscosity of the bone cement by allowing more or less time before initiating the compressing and dispensing operation referred to hereinabove.

Following the aforementioned waiting period, according to a preferred embodiment of the invention, the user causes primary membrane seal 101 to be ruptured by twisting knife mounting collar 117 of device 100 shown in FIG. 1, by a quarter turn. Primary membrane seal 101 may, according to one embodiment of the invention, be ruptured by using, for example, a micro serrated blade to pierce primary membrane seal 101. Such a blade is depicted as knife blade 122, shown mounted in knife blade collar 117 in FIG. 1.

According to the illustrative embodiment of the invention depicted in FIG. 1, primary membrane seal 101 is positioned proximal to plunger 124, in-between the two component chambers and plunger 124. Alternatively, primary membrane seal 101 may be positioned distal to the plunger.

The purpose of primary membrane seal 101, which may, for example, be realized by a co-extruded or laminated film on the outside surface of plunger 124, is to prevent plunger 124 from being drawn into evacuated mixing chamber 123 and also prevent loss of vacuum from evacuated mixing chamber 123.

Another seal is called for in a preferred embodiment of the invention, namely 0-ring plunger seal 119 as depicted in FIG. 1. 0-ring plunger seal 119, which may be realized by use of a rubber 0-ring seal, serves to seal the vacuum in evacuated mixing chamber 123 while the apparatus depicted in FIG. 1 is being store; and keeps the mix contained in mixing chamber 123 when device 100 depicted in FIG. 1 is in use.

Next, the entire assembly depicted in FIG. 1 is, according to the teachings of the invention, placed into a dispensing gun (not shown) and the contents are compressed by the gun to facilitate completing the mixing process and initiate the dispensing process contemplated herein. An example of a commercially available dispensing gun suitable for use in conjunction with device 100 depicted in FIG. 1 is the Howmedica Enhanced Bone Cement Gun, Model 6205-1-500.

The compression of the mixture serves as a vehicle for insuring a good, homogeneous mixture of the powder and monomer liquid before the cement is dispensed. For example, air trapped between the particles of stored powder and subsequently introduced into the mixture may be reduced through the compression that takes place as plunger head 124 is forced toward membrane seal 116 by the gun pressing on block 125.

Eventually, the force applied by the gun will cause membrane seal 116 (located at the distal end of mixing chamber 123) to be ruptured by the pressure of the plunger 124 compressing the mixture. When this occurs, passageway 201 is opened, as shown in FIG. 2, through which the prepared cement may flow from evacuated mixing chamber 123.

For dispensing the polymerized cement mixture, the user continues to trigger the gun, forcing the mixture out through passageway 201 at a rate desirable to the user.

As indicated hereinbefore, FIG. 2 is a partial elevational sectional view of device 200 (corresponding to device 100 depicted in FIG. 1) after the cement has been prepared and been substantially dispensed from device 200. Portions of seal 116 from FIG. 1 (shown ruptured in FIG. 2) are indicated by seal portions 216a and 216b in FIG. 2; along with a volume of cement 202 being dispensed through passageway 201.

FIG. 2 also depicts plunger head 224 (corresponding to plunger head 124 of FIG. 1) at the distal end of what was formerly evacuated mixing chamber 123 of FIG. 1, at the completion of the compression and dispensing processes.

Further reference should be made to FIG. 1 to note that plunger head 124 functions to support most of the components of the depicted device 100. Furthermore, it should be understood that plunger head 124 is designed in combination with the components used in any given device fabricated in accordance with the teachings set forth herein, to, for example, support and orient preselected diffusion means to enable the components being mixing to interact at a predetermined distance within evacuated mixing chamber 123, etc.

According to the embodiment of the invention depicted in FIG. 1, plunger head 124 also includes a knife edge, shown as scraper blade 118, which functions to scrape the cement mix from the walls of evacuated mixing chamber 123 during the cement dispensing process. Scraper blase 118 also serves to prevent highly viscous mixtures from working past the plunger during the compression phase of the mixing and dispensing processes.

Still further, with reference to FIG. 1, it should be noted that plunger head 124 is preferably designed to have the depicted conical shape when used in conjunction with an evacuated mixing chamber having a conical shaped distal end, such as the mixing chamber depicted in FIG. 1. This design match enables the maximum amount of cement to be forced through passageway 201 (depicted in FIG. 2), in the manner described hereinabove. A suitable material for fabricating plunger head 124 is molded polyethylene.

The plunger head used in device 100 depicted in FIG. 1 (plunger head 124) is in and of itself believed to be novel and includes, as shown and described hereinabove, means for simultaneously injecting the contents of the first and second component chambers into the mixing chamber vacuum, in combination with means for uniformly mixing the powdered component and the liquid component within the mixing chamber.

Reference should now be made to FIG. 3 which is a cross sectional view of device 100 depicted in FIG. 1, taken along section line A—A, illustrating the orientation of monomer and powder chambers, 103 and 102 respectively, with respect to each other and knife blade collar 117. These components are designated as 300, 303, 302 and 317 in FIG. 3, respectively.

It can be seen with reference to FIG. 3 that, as previously indicated, one embodiment of the invention contemplates that chambers 302 and 303 be joined together tangentially along their exterior surfaces. This is indicated at 350 in FIG. 3 and corresponds to reference numeral 150 of FIG. 1. Alternate embodiments of the invention do not require this orientation of cylinders or even cylinder cross sections matching those depicted. For example, embodiments of the invention are envisions where space limitations within the chamber, component volume requirements, etc., may call for cylinders having different shapes (for example kidney shapes), and/or cylinders which do not touch one another within the chamber, etc.

It can also be seen with reference to FIG. 3 that, along section A—A as shown in FIG. 1, both chambers are located within knife blade collar 317, and that seals 306 and 307 (corresponding to seals 106 and 107 of FIG. 1, respectively) are visible at the distal end of the component chambers.

Reference should now be made to FIG. 4 which is a cross sectional view of device 100 depicted in FIG. 1, taken along section line B—B, illustrating the orientation of the monomer and powder diffuser nozzles 114 and 115, respectively, incorporated in plunger head 124 contemplated by the invention, with the view of plunger head 124 being that seen from the evacuated mixing chamber 123 side of device 100 looking back toward the base of the aforementioned knife blade collar 117. These components are designated as 414, 415, 424, 423, 400 and 417 in FIG. 4, respectively.

It can be seen with reference to FIG. 4 that, according to a preferred embodiment of the invention, diffuser nozzles 414 and 415 are oriented at right angles. This is indicated by the orientation of nozzle outlets 450 and 451 shown in FIG. 4.

Although not intended to be a limitation on the nozzle orientation chosen for a particular application, the aforementioned orientation has been found to help achieve an improved bone cement mixture, when using the methods and apparatus contemplated by the invention in the manner taught herein, by evenly distributing the components within evacuated mixing chamber 424 and minimizing the potential for poymerized powder from occluding the nozzle outlets.

Finally, it should be noted (and those skilled in the art will readily appreciate), that an improved cement product is formed by the processes described herein. Accordingly, any products of the aforementioned processes (including non-cementitious products) are meant to be included within the scope of the present invention.

What has been described in detail hereinabove are methods and apparatus meeting all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

For example, the methods and apparatus described herein were presented in the context of preparing a bone cement from a powdered polymer and liquid monomer component. However, those skilled in the art will readily appreciate that such methods and apparatus are well suited for mixing other powdered and liquid components, in application that are unrelated to the preparation of bone cement, using the vacuum injection system, plunger head design, etc., taught herein.

The embodiments and examples set forth herein were presented in order to best explain the principles of the instant invention and its practical application to thereby enable others skilled in the art to best utilize the instant invention in various embodiments and with various modifications as are suited to the particular use contemplated.

It is, therefore, to be understood that the claims appended hereto are intended to cover all such modifications and variations which fall within the true scope and spirit of the invention.

What is claimed is:

1. A plunger head for use as part of a system for mixing and delivering a powdered component of bone cement, stored in a first chamber attached to the proximate end of said plunger head, with a liquid component of bone cement, stored in a second chamber attached to the proximate end of said plunger head, within an evacuated mixing chamber into which the distal end of said plunger head extends, comprising:
    (a) means for simultaneously injecting the contents of said first and second component chambers into said mixing chamber vacuum; and
    (b) means for uniformly mixing said powdered component and said liquid component at a predetermined distance within said mixing chamber thereby saturating said powdered component with said liquid component.

2. Apparatus as set forth in claim 1 wherein said means for simultaneously injecting further comprises means for simultaneously subjecting the contents of said first and second component chambers to the effects of the mixing chamber vacuum.

3. Apparatus as set forth in claim 2 wherein said means for simultaneously subjecting the contents of said first and second component chambers to the effects of said mixing chamber vacuum further comprises the combination of timing step means, seal piercing means and component diffusion means to simultaneously open (a) a first passageway through said plunger head between said first component chamber and said evacuated mixing chamber, and (b) a second passageway through said plunger head between said second component chamber and said evacuated mixing chamber.

4. Apparatus as set forth in claim 3 wherein said combination is further operative to first break a seal associated with each of said first and second component chambers and then simultaneously break seals associated with said evacuated mixing chamber to thereby enable said powdered component and said liquid component to be simultaneously drawn from said first and second component chambers, through said first and second passageways respectively, into said evacuated mixing chamber.

5. Apparatus as set forth in claim 3 wherein said component diffusion means comprises a first one way nozzle, operative to broadcast said powdered component into said mixing chamber, and a second one way nozzle, operative to spray said liquid component into said mixing chamber.

6. Apparatus as set forth in claim 5 wherein said component diffusion means is further to operative to prevent component and mixture backflow.

7. A mixing device, used as part of a system for mixing powdered and liquid bone cement components and delivering the bone cement mix, comprising:
    (a) a first evacuated container;
    (b) a second container containing a powdered component of bone cement;
    (c) a third container containing a liquid component of bone cement; and
    (d) means for simultaneously connecting said second and third containers to said first container allowing said powdered component and said liquid component to be simultaneously drawn into said first container by the vacuum therein, and be uniformly mixed within said first container by saturating said powdered component with said liquid component at a predetermined distance within said mixing chamber.

8. The mixing device of claim 7 further including means for dispensing said bone cement mix.

9. The mixing device of claim 8 wherein said first container is cylindrical in shape and has a first end with a dispensing nozzle and said means for dispensing is a plunger slidably mounted within a second open end of said cylindrical first container.

10. The mixing device as set forth in claim 8 wherein said first container has a breakable seal formed thereon for retaining the evacuated condition thereof.

11. The mixing device as set forth in claim 8 wherein said second and third containers have means for allowing atmospheric pressure to act thereon to force said powder and liquid into said first container upon the simultaneous connection of said second and third containers to said evacuated first container.

12. Apparatus for preparing and delivering a self curing bone cement formed as a polymeric reaction product when a powdered polymer component of bone cement is mixed with a liquid monomer component of bone cement, comprising:
    (a) a first component chamber for storing said powdered polymer component;

(b) a second component chamber for storing said liquid monomer component;
(c) an evacuated mixing chamber;
(d) means for simultaneously injecting said powdered polymer component and said liquid monomer component into said evacuated mixing chamber; and
(e) means for uniformly mixing the components at a predetermined distance within said mixing chamber thereby saturating said powdered polymer component with said liquid monomer component.

13. Apparatus as set forth in claim 12 wherein said means for simultaneously injecting further comprises means for simultaneously subjecting the contents of said first and second component chambers to the effects of the mixing chamber vacuum.

14. Apparatus as set forth in claim 13 wherein said means for simultaneously subjecting the contents of said first and second component chambers to the effects of the mixing chamber vacuum further comprises the combination of timing step means, seal piercing means and component diffusion means to simultaneously open (a) a first passageway between said first component chamber and said evacuated mixing chamber, and (b) a second passageway between said second component chamber and said evacuated mixing chamber.

15. Apparatus as set forth in claim 14 wherein said combination is further operative to first break a seal associated with each of said first and second component chambers and then simultaneously break seals associated with said evacuated mixing chamber to thereby enable said powdered polymer component and said liquid monomer component to be simultaneously drawn from said first and second component chambers, through said first and second passageways respectively, into said evacuated mixing chamber.

16. Apparatus as set forth in claim 14 wherein said component diffusion means comprises a first one way nozzle, operative to broadcast said powdered polymer component into said mixing chamber, and a second one way nozzle, operative to spray said liquid monomer component into said mixing chamber.

17. Apparatus as set forth in claim 16 wherein said component diffusion means is further to operative to prevent component and mixture backflow.

18. Apparatus as set forth in claim 16 further comprising means for pressurizing the cement mixture in said mixing chamber to compress air out of said cement mixture.

19. Apparatus as set forth in claim 18 further comprising means for dispensing the compressed cement mixture from said mixing chamber.

20. Apparatus as set forth in claim 19 wherein said means for dispensing comprises a plunger head that includes said combination of timing step means, seal piercing means and component diffusion means.

21. Apparatus as set forth in claim 20 further comprises a means for exerting a compressive force on said plunger head to pressurize and dispense said cement mixture.

22. Apparatus as set forth in claim 21 wherein said means for exerting a compressive force is a caulking gun.

23. Apparatus for saturating a predetermined quantity of a powdered component of bone cement with a predetermined volume of a liquid component of bone cement as part of a component mixing and mixed cement delivery process, comprising:
(a) means for simultaneously injecting said powdered component and said liquid component into a mixing chamber, wherein said means for simultaneously injecting includes diffusion means to broadcast said powdered component and spray said liquid component into said chamber; and
(b) means for causing said powdered component and said liquid component to interact at a predetermined distance within said chamber.

24. Apparatus as set forth in claim 23 wherein said means for simultaneously injecting is a vacuum operated injection system.

* * * * *